United States Patent [19]

Jones et al.

[11] Patent Number: 4,637,749

[45] Date of Patent: Jan. 20, 1987

[54] CONNECTOR FOR MODULAR PHYSIOLOGICAL INSTRUMENTS

[75] Inventors: Paul W. Jones, Issaquah; Rodney J. Merry, Bothell; Gregory A. Linstad, Woodinville, all of Wash.

[73] Assignee: Physio-Control Corporation, Redmond, Wash.

[21] Appl. No.: 689,743

[22] Filed: Jan. 8, 1985

[51] Int. Cl.$^4$ .................... F16B 21/00; E04G 4/00
[52] U.S. Cl. ...................... 403/322; 403/325; 403/330; 403/340; 403/380; 248/222.1
[58] Field of Search .............. 403/376, 322, 321, 330, 403/364, 380, 339, 340, 331, 327, 325, 341; 248/225.1, 222.1; 211/192; 350/96.23, 96.17; 128/710

[56] References Cited

U.S. PATENT DOCUMENTS

| | | | |
|---|---|---|---|
| 709,400 | 9/1902 | Fitzpatrick | 403/341 |
| 838,767 | 12/1906 | Bradley | 403/325 |
| 1,018,556 | 2/1912 | Engle | 403/376 |
| 2,682,414 | 6/1954 | Richardson | 403/325 |
| 3,608,935 | 9/1971 | Hodapp, Jr. | 403/322 |
| 3,857,619 | 12/1974 | Adickes . | |
| 4,097,113 | 6/1978 | McKelvy . | |
| 4,135,783 | 1/1979 | Kunze | 350/96.17 |
| 4,140,356 | 2/1977 | Chervanak . | |
| 4,221,430 | 9/1980 | Frobose . | |
| 4,318,395 | 3/1982 | Tawara | 403/322 |
| 4,384,742 | 5/1983 | Wisniewski . | |
| 4,429,949 | 2/1984 | Cartier | 350/96.23 |

Primary Examiner—Cornelius J. Husar
Assistant Examiner—Peter M. Cuomo
Attorney, Agent, or Firm—Christensen, O'Connor, Johnson & Kindness

[57] ABSTRACT

An apparatus for connecting first and second physiological instrument components. The first component has an exterior first surface, and the second component has an exterior second surface. The apparatus comprises means forming a plurality of mutually parallel blades extending outward at the first surface at an acute angle with respect to a direction normal to the first surface, and means forming a plurality of mutually parallel slots extending inwardly at the second surface at the acute angle with respect to a direction normal to the second surface. The slots are sized and spaced to receive the blades to thereby connect the components. Latch means are provided for selectively latching one of the blades in its corresponding slot, and for preventing unlatching of the components when only one of the components is supported. In a preferred embodiment, the acute angle is approximately 75°.

16 Claims, 8 Drawing Figures

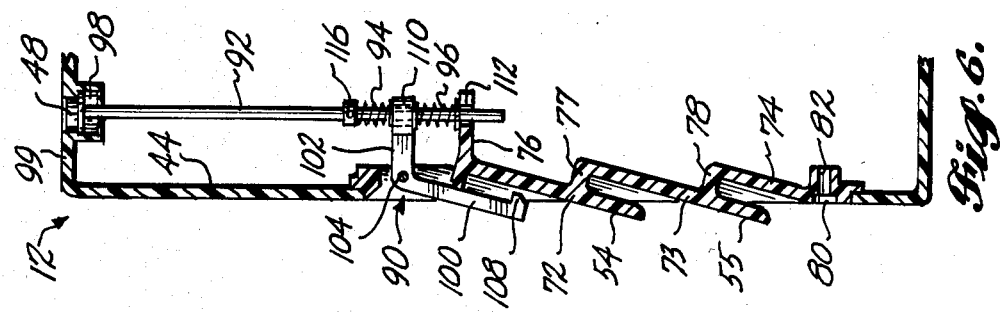
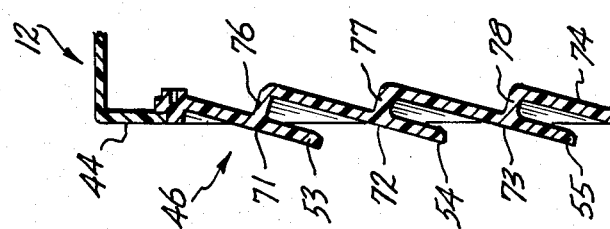
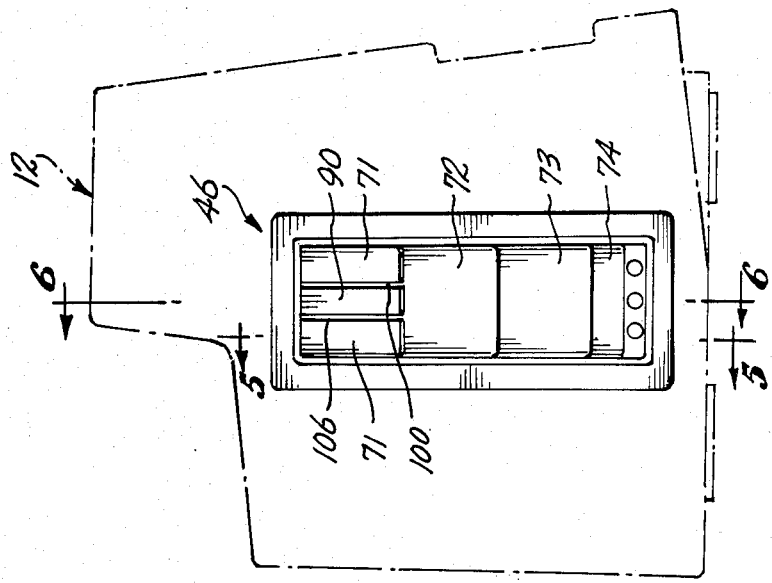
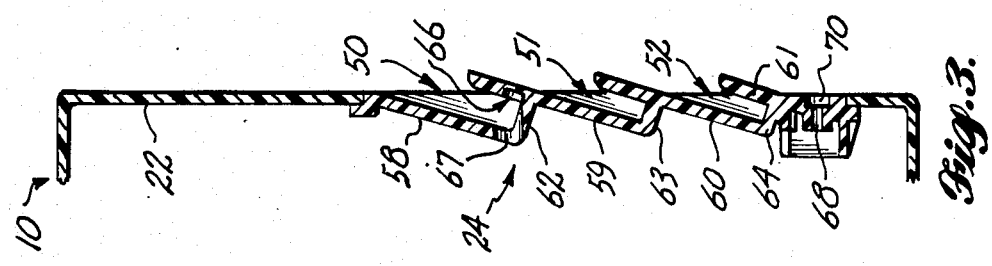

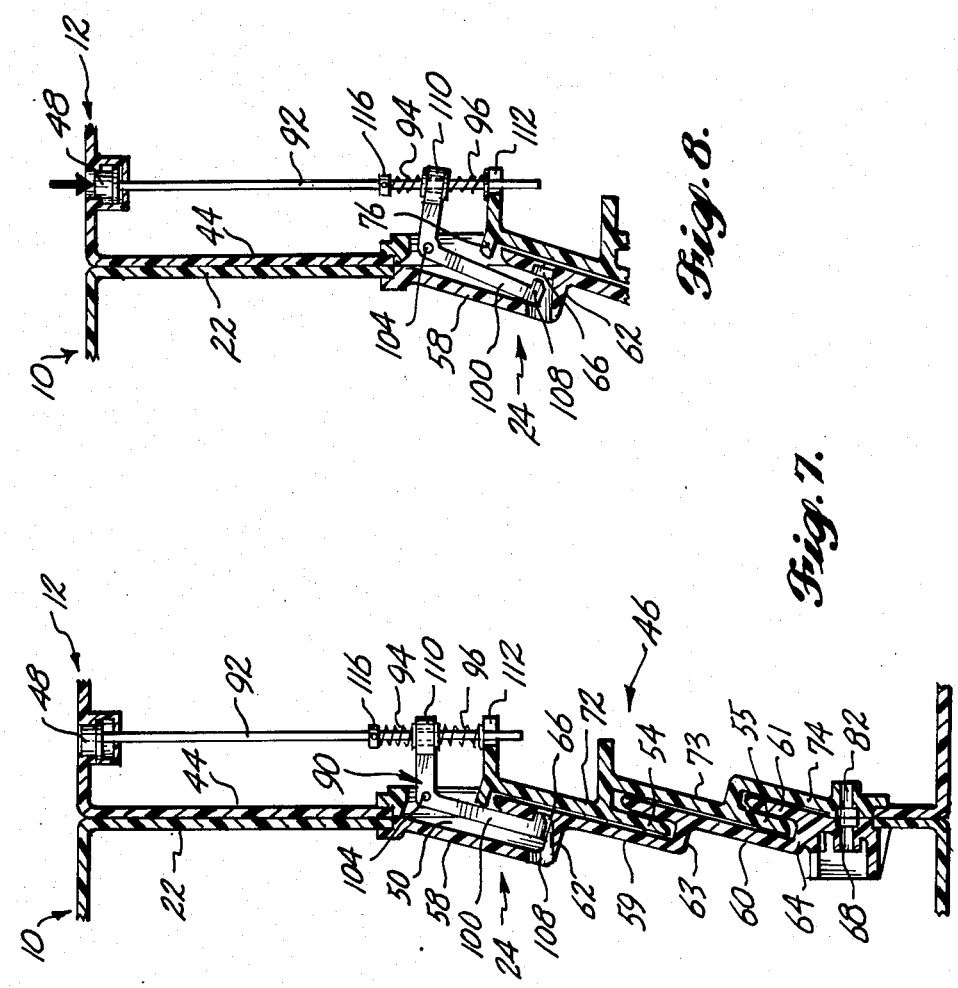

CONNECTOR FOR MODULAR PHYSIOLOGICAL INSTRUMENTS

FIELD OF THE INVENTION

This invention generally relates to modular physiological instruments, and more particularly, to an improved mechanical connector for such instruments.

BACKGROUND OF THE INVENTION

An ECG monitor is an instrument for providing a real-time or delayed display and/or a printed record of a patient's ECG waveform. The ECG monitor is interconnected with the patient by means of a set of electrodes and associated conductors commonly referred to as a patient cable. The ECG waveform is typically displayed by means of a cathode ray tube (CRT), and the printed record is typically provided by means of a strip-chart recorder or its equivalent. An ECG monitor is a diagnostic instrument, i.e., it assists the operator in evaluating the physiological condition, and in particular the cardiac condition, of the patient.

A defibrillator is a therapeutic instrument particularly useful in conjunction with an ECG monitor to assist in curing certain cardiac irregularities, particularly ventricular and atrial fibrillation. The defibrillator is typically interconnected with the patient via a set of large paddle electrodes and associated conductors, and operates to apply a high energy DC pulse to the patient via the paddle electrodes when appropriately triggered by an operator.

In one type of prior physiological instrument, an ECG monitor and a defibrillator are combined and electrically connected within a single housing. In such an instrument, circuitry is generally provided to allow the ECG monitor to be connected to the patient through the paddle electrodes that are normally associated with the defibrillator. Physiological instruments are also known in which the ECG monitor and defibrillator are modular components that are capable of operating either independently, or in an interconnected manner in which the defibrillator is mechanically and electrically connected to the ECG monitor.

The mechanical connection between the modular components of an ECG monitor/defibrillator instrument, i.e., between the ECG monitor and the defibrillator, is an important feature of such an instrument. For example during routine use in a hospital, the instrument is usually operated with the ECG and defibrillator modules connected. However, emergency situations can arise in which it is necessary to rapidly transport the defibrillator to another part of the hospital, or to a location outside the hospital. The mechanical connection between the defibrillator and the ECG monitor must therefore permit rapid separation of the units, in spite of the fact that the units may be comparatively heavy. However, the mechanical connection must also be rigid when separation is not desired, and must permit the combined instrument to be picked up by lifting only one of the components, without risk of separation.

SUMMARY OF THE INVENTION

The present invention provides an apparatus for mechanically connecting two components in such a way that separation of the components may be accomplished by a single upward and outward motion of one of the components. The mechanical connector of the present invention also provides effective means for ensuring that the components will not become inadvertently separated when the combined instrument is held by only one component.

In one aspect, the present invention provides an apparatus for connecting first and second physiological instrument components that include exterior first and second surfaces respectively. The apparatus comprises means forming a plurality of mutually parallel blades extending outward at the first surface at an acute angle with respect to a direction normal to the first surface, and means forming a plurality of mutually parallel slots extending inwardly at the second surface at said acute angle with respect to a direction normal to the second surface. The slots are sized and spaced from one another to receive the blades to connect the components. Latch means comprising a latch arm are also provided to permit selective latching of one of the blades in its corresponding slot. The latch means may also comprise an actuator coupled to the latch arm by a resilient member, the stiffness of the resilient member being selected such that when the combined instrument is supported by only one component, movement of the actuator is insufficient to unlatch the components.

In another aspect, the present invention comprises an apparatus for connecting first and second physiological instrument components that have respective first and second exterior surfaces. The apparatus comprises first connector means comprising a plurality of mutually parallel first planar members, and second connector means comprising a plurality of mutually parallel second planar members. Each first planar member extends upward and outward at the first surface at an acute angle with respect to a direction normal to the first surface. The first planar members are spaced apart along a line parallel to the first surface to form a plurality of first slots. Each second planar member extends downward and outward at the second surface at said acute angle with respect to a direction normal to the second surface. The second planar members are spaced apart along a line parallel to the second surface to form a plurality of second slots. The first and second planar members are dimensioned and spaced from one another such that the outer ends of the first planar members can be received in the second slots while the outer ends of the second planar members are received in the first slots, to thereby connect the components. The apparatus may further comprise optical signalling means positioned in the first and second surfaces for providing communication between the components when the components are connected.

BRIEF DESCRIPTION OF THE DRAWINGS

FIG. 3 is a cross-sectional view of a portion of the ECG monitor showing the connector of the present invention;

FIG. 4 is a side elevational view of the defibrillator;

FIG. 5 is a partial cross-sectional view taken along the line 5—5 of FIG. 4;

FIG. 6 is a partial cross-sectional view taken along the line 6—6 of FIG. 4;

FIG. 7 is a cross-sectional view showing the defibrillator joined to the ECG monitor; and FIG. 8 is a partial cross-sectional view showing the unlatching of the connectors.

DETAILED DESCRIPTION OF THE INVENTION

Figure 1:
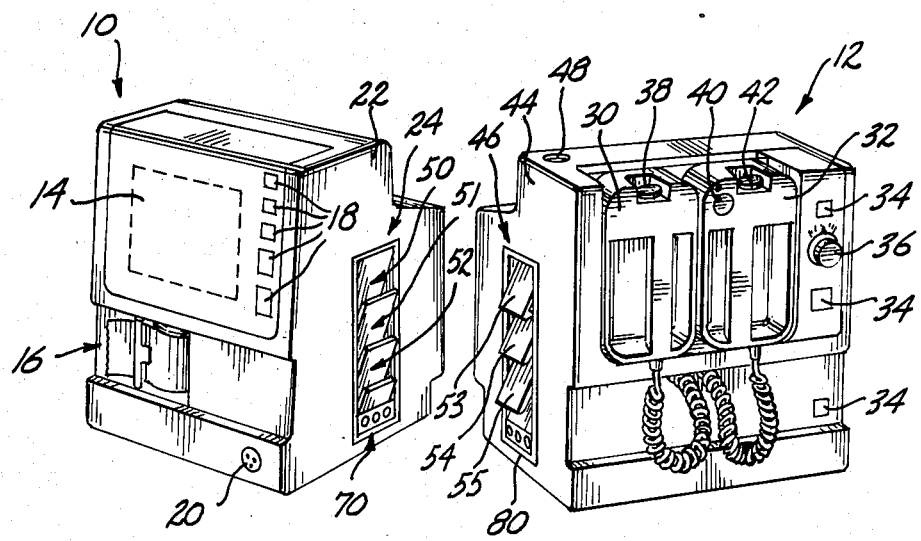
FIG. 1 is a perspective view of a separated ECG monitor and defibrillator that include the mechanical connector for the present invention.

FIG. 1 illustrates a modular physiological instrument comprising ECG monitor 10 and defibrillator 12 that may be joined by means of the mechanical connector of the present invention. ECG monitor 10 comprises display screen 14, recorder 16, switches 18 and connector 20 for receiving a patient cable. ECG monitor 10 also includes side 22 having connector 24 mounted or formed therein. Defibrillator 24 comprises paddle electrodes 30 and 32, switches 34, and energy selector dial 36. Paddle electrode 32 includes charge switch 40, and paddle electrodes 30 and 32 include discharge switches 38 and 42 respectively. The defibrillator may be used by pressing charge switch 40, waiting until the defibrillator energy storage means has charged, applying paddle electrodes 30 and 32 to a patient, and then simultaneously depressing discharge switches 38 and 42. As indicated in FIG. 1, electrodes 30 and 32 are stowed in a compartment in the upper face of the defibrillator. The defibrillator also comprises side 44 having connector 46 mounted or formed therein, and actuator 48 recessed in the upper surface of the defibillator. The purpose of actuator 48 is described below.

Connector 24 of ECG monitor 10 is shaped so as to form slots 50-2, and connector 46 of defibrillator 12 is shaped so as to form blades 53-55. Slots 50-52 are oriented parallel to one another and are inclined at an acute angle (i.e., an angle greater than zero and less than 90°) with respect to the horizontal direction. In the embodiment illustrated in FIG. 1, slots 50-52 are oriented at an angle of approximately 75° with respect to the horizontal, i.e., at an angle of 15° with respect to side 22 of ECG monitor 10. Blades 53-55 are parallel to one another and are oriented at an angle identical to the angle of slots 50-52. Blades 53-55 are dimensioned and spaced such that they can be inserted into slots 50-52, respectively, and such that when the blades are inserted into the slots, there is no play between the blades and slots. Defibrillator 12 may therefore be rigidly connected to ECG monitor 10 by positioning the instruments with their respective sides 22 and 44 adjacent to one another and with defibrillator 12 slightly elevated with respect to ECG monitor 10, and then lowering the defibrillator such that blades 53-55 slide downward and inward into slots 50-52. The reverse motion is used to separate the instruments. As described below, separation can only be accomplished by applying downward pressure on actuator 48.

Connector 24 further comprises windows 70 positioned in the lower part of the connector beneath slot 52. Connector 46 comprises a similar set of windows 80 positioned in the lower part of connector 46 beneath blade 55. As indicated below, windows 70 and 80 may be used for the transmission of optical signals between the ECG monitor and the defibrillator including timing and control signals, physiological data signals and instrument state signals.

Referring now to FIG. 3, connector 24 of ECG monitor 10 comprises side sections 58-61 and end sections 62-64. Side section 58, end section 62 and the upper portion of side section 59 combine to form slot 50. The lower portion of side section 59, end section 63 and the upper portion of side section 60 combine to form slot 51. The lower portion of side section 60, end section 64 and side section 61 combine to form slot 52. Each side section is oriented at an angle of 15° with respect to side 22 of ECG monitor 10. The upper portion of side section 59 includes recess 66 on its inner face immediately above the junction with end section 62. The purpose of recess 66 is described below. Access hole 67 is provided for forming recess 66. The lower portion of connector 24 below end section 64 includes window 70 behind which optical element 68 is mounted. Optical element 68 may comprise an LED, phototransistor or similar element, and may be used to establish optical communication between the ECG monitor and the defibrillator when these components are mechanically connected.

Referring now to FIGS. 4-6, connector 46 of defibrillator 12 comprises side sections 71-74 and end sections 76-78. The lower portion of side section 71 comprises blade 53, the lower portion of side section 72 comprises blade 54, and the lower portion of side section 73 comprises blade 55. The lower portion of connector 46 may include optical element 82 mounted behind window 80. Optical element 82 is adapted to cooperate with optical element 68 in ECG monitor 10 to establish optical communication between the components when they are mechanically connected.

As may be seen by comparing FIGS. 3 and 5, connector 46 is complementary to connector 24. Thus the designation of elements 50-52 as slots and 53-55 as blades is simply one possible description, and the connectors could just have well been described, for example, by designating the upper portion of side section 60 as a blade and by designating the recess between side sections 72 and 73 and end section 77 as a slot. For all blade/slot arrangements and descriptions, the thickness of the blades should be equal to the thickness of the slots, with the exception described below, such that when the blades are inserted into the slots, there is no play between the blades and slots, and therefore no looseness to the connection between the ECG monitor and the defibrillator.

Figure 2:
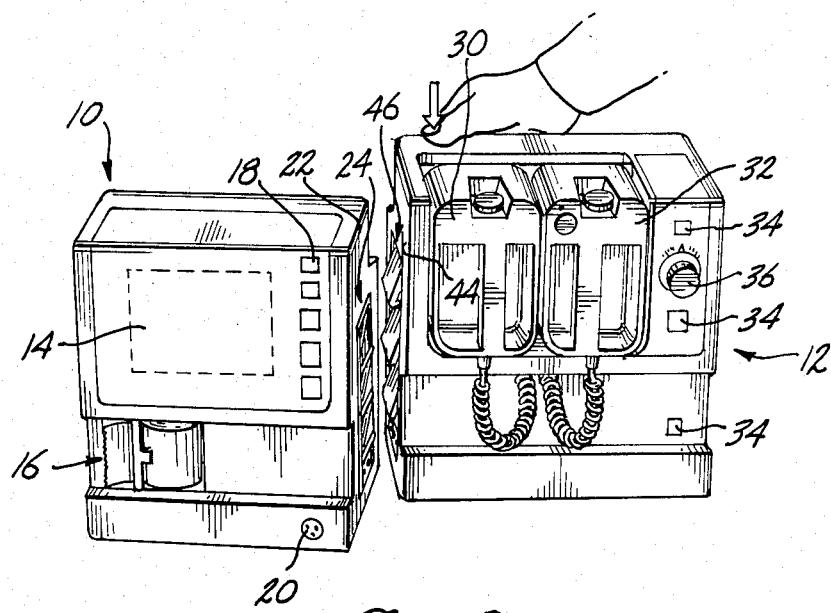
FIG. 2 is a perspective view illustrating the separation of the defibrillator from the ECG monitor.

The orientation of side sections 58-61 and 71-74 should be selected based upon the usage of the components that they are designed to interconnect. For the illustrated embodiment in which the connectors are used to connect an ECG monitor and a defibrillator, side sections 58-60 of connector 24 should be inclined upward and outward with respect to the ECG monitor, and side sections 71-74 of connector 46 should be angled downward and outward with respect to the defibrillator. Separation of the components may thereby be accomplished by lifting upward on the defibrillator while the ECG monitor remains stationary, as indicated in FIG. 2. The upper rear surface of defibrillator 12 preferably includes a recess (not shown) for receiving the fingers of an operator's hand. In a preferred embodiment, side sections 58-61 of connector 24 of ECG monitor 10 extend upward and outward at an acute angle of greater than 45° with respect to the horizontal, and side sections 71-74 of connector 46 of defibrillator 12 extend downward and outward at an identical angle to that of side sections 58-61. The force required to separate the components is then primarily an upward pull on the defibrillator. In the most preferred embodiment for an instrument comprising an ECG monitor and a defibrillator, the acute angle is approximately 75°, such an angle having been found to provide an optimum combination of ease of separation and reconnection and rigidity.

After the ECG monitor and defibrillator components have been mechanically connected, unintentional separation of the components is prevented by a latching mechanism that comprises latch arm 90, rod 92, springs 94 and 96, and actuator 48. Latch arm 90 comprises lower arm 100 and upper arm 102 that are oriented at an angle of approximately 90° with respect to one another. The latch arm is mounted at pivot 104 for rotation in the plane of the drawing of FIG. 6. As indicated in FIG. 4, lower arm 100 is positioned within slot 106 formed in side section 71 of connector 46. Lower arm 100 has the same general cross section as side section 71, but includes projection 108 that extends toward defibrillator 12 from the lowermost portion of lower arm 100. As illustrated in FIG. 3, end section 62 is longer than end sections 63 and 64, with the result that slot 50 has a greater thickness than slots 51 or 52. Such extra thickness is provided to accommodate the latching and unlatching mechanism described below in connection with FIGS. 6-8. Upper arm 102 of latch arm 90 includes collar 110 that encircles but does not grip rod 92. The upper end of rod 92 is connected to actuator 48 that is positioned for up and down reciprocal motion in recess 98 in the upper surface 99 of the defibrillator. The lower end of rod 92 passes through spring 94, collar 110, spring 96 and guide 112, guide 112 being an inward extension of end section 76. Spring 96 is constrained against axial movement by collar 110 and guide 112. Spring 94 is constrained against axial movement by collar 110 and by stop 116 secured to rod 92.

FIGS. 6-8 illustrate the operation of the latching mechanism. As illustrated in FIG. 7, when the components are mechanically connected, lower arm 100 is positioned in slot 50, and projection 108 engages recess 66 formed in the upper portion of side section 59. In this position, lower arm 100 and side section 71 are secured in recess 50, and the components cannot be separated. Spring 96 provides an upward force on collar 110 that tends to rotate latch arm 90 such that lower arm 100 abuts end section 76, and projection 108 thereby remains engaged in recess 66. The combined instrument may therefore be lifted by picking up defibrillator 12 without supporting the ECG monitor. Separation of the components may be effected by depressing actuator 48 while both components are supported, and then lifting upward on defibrillator 12. Downward movement of actuator 48 is transmitted through rod 92, stop 116 and spring 94 to collar 110. The stiffness of spring 94 is selected such that the downward movement indicated in FIG. 8 is sufficient to rotate latch arm 90, against the force of spring 96, to a position in which projection 108 is clear of recess 66. In this position, the components may be separated by means of an upward and slightly outward pulling force on defibrillator 12. Once the components have been separated and actuator 48 released, the latching mechanism returns to the position shown in FIG. 6.

When the combined instrument is lifted by picking up or supporting only the defibrillator, the weight of the ECG monitor results in a force that tends to pull side section 59 downward with respect to lower arm 100. This downward force in turn results in a frictional force between projection 108 and side section 59 that resists rotation of latch arm 90 about pivot 104. The stiffness of spring 94 is selected to be small enough such that when actuator 48 is depressed while the combined instrument is supported by the defibrillator only, the downward motion of rod 92 is accommodated entirely by compression of spring 94 without any rotation of latch arm 90. Thus, accidental separation of the components when the ECG monitor is unsupported is not possible, even when actuator 48 is depressed.

While the preferred embodiments of the invention have been illustrated and described, it should be understood that variations will be apparent to those skilled in the art. Accordingly, the invention is not to be limited to the specific embodiments illustrated and described, and the true scope and spirit of the invention are to be determined by reference to the following claims.

The embodiments of the invention in which an exclusive property or privilege is claimed are defined as follows:

1. An apparatus for connecting first and second physiological instrument components, the first component having an exterior first surface and the second component having an exterior second surface, the apparatus comprising:
   means forming a plurality of mutually parallel blades extending outward at the first surface at an acute angle with respect to a direction normal to the first surface;
   means forming a plurality of mutually parallel slots extending inwardly at the second surface at said acute angle with respect to a direction normal to the second surface, the slots being sized and spaced to receive the blades to thereby connect the components; and
   latch means for selectively engaging and securing one of the blades in its corresponding slot such that the blade cannot be removed from the slot without disengaging the latch means from the blade.

2. The apparatus of claim 1, wherein said acute angle is approximately 75°.

3. The apparatus of claim 1, wherein the thickness of the slots in a direction normal to said acute angle is substantially equal to the thickness of the blades in said direction, such that when the blades are received in the slots, there is not play therebetween.

4. The apparatus of claim 1, wherein the latch means comprises a latch arm pivotally mounted for rotation between a latching position in which the said one blade is held in the corresponding slot, and an unlatched position in which said one blade can be moved out of the corresponding slot.

5. The apparatus of claim 4, wherein the latch means further comprises a return spring adapted to exert a force on the latch arm tending to move the latch arm to the latched position.

6. The apparatus of claim 5, wherein the blades extend outward and downward at the first surface at said acute angle and the slots extend downward and inward at the second surface at said acute angle, and wherein the latch means further comprises an actuator coupled to the latch arm by a resilient member, the stiffness of the resilient member being selected such that when the first component is supported while the second component is unsupported, movement of the actuator is insufficient to overcome the frictional force holding the latch arm in the latching position.

7. An apparatus for connecting first and second physiological instrument components, the first component having an exterior first surface and the second component having an exterior second surface, the apparatus comprising:
   first connector means comprising a plurality of mutually parallel first planar members and first cross members, each first planar member extending upward and outward at the first surface at an acute angle with respect to a direction normal to the first surface, the first planar members being spaced apart along a line parallel to the first surface, each first cross member joining the end of one first planar member to a point intermediate the ends of an adjacent first planar member so as to form a plurality of first slots;

second connector means comprising a plurality of mutually parallel second planar members and second cross members, each second planar member extending downward and outward at the second surface at said acute angle with respect to a direction normal to the second surface, the second planar members being spaced apart along a line parallel to the first surface, each second cross member joining a point intermediate the ends of one second planar member to the end of the adjacent second planar member so as to form a plurality of second slots;

the first and second planar members being dimensioned and spaced from one another such that the outer ends of the first planar members can be received in the second slots while the outer ends of the second planar members are received in the first slots, to thereby connect the components; and said second compoennt comprising latch means including a latch arm, an actuator, and a resilient member connecting the actuator to the latch arm, the latch arm being mounted for rotation to and from a latching position in which the latch arm engages one of the first planar members when said one first planar member is received in one of the second slots, the stiffness of the resilient member being selected such that when the second component is supported and the first component is unsupported, movement of the actuator is insufficient to overcome the frictional engagement between the latch arm and said one first planar member.

8. The apparatus of claim 7, wherein the acute angle is approximately 75°.

9. The apparatus of claim 7, wherein the thickness of the first and second planar members is substantially equal to the distance between adjacent planar members in a direction normal to said acute angle, such that when the outer ends of the first planar members are received in the second slots and the outer ends of the second planar members are received in the first slots, there is no play between the planar members.

10. The apparatus of claim 7, further comprising optical signalling means positioned in the first and second surfaces for providing communication between the components when the components are connected.

11. A physiological instrument comprising:
a first component having a vertically oriented first exterior surface;
a second component having a vertically oriented second exterior surface;
means in said first component forming a plurality of mutually parallel blades extending outward at the first exterior surface at an acute angle with respect to a direction normal to the first exterior surface;
means in said second component forming a plurality of mutually parallel slots extending inwardly at the second exterior surface at said acute angle with respect to a direction normal to the second exterior surface, the slots being sized and spaced to receive the blades to thereby connect the components; and
said second component further comprising a latch means for selectively engaging and securing one of the blades in its corresponding slot such that the blade cannot be removed from the slot without disengaging the latch means for the blade.

12. The instrument according to claim 11, wherein said acute angle is approximately 75°.

13. The apparatus of claim 11, wherein the latch means comprises a latch arm pivotally mounted for rotation between a latching position in which said one blade is held in the corresponding slot, and an unlatched position in which said one blade can be moved out of the corresponding slot.

14. The apparatus of claim 13, wherein the latch means further comprises a return spring adapted to exert a force on the latch arm tending to move the latch arm to the latched position.

15. The apparatus of claim 14, wherein the blades extend outward and downward at the first exterior surface at said acute angle and the slots extend downward and inward at the second exterior surface at said acute angle, and wherein the latch means further comprises an actuator coupled to the latch arm by a resilient member, the stiffness of the resilient member being selected such that when the first component is supported while the second component is unsupported, movement of the actuator is insufficient to overcome the frictional force holding the latch arm in the latching position.

16. An apparatus for connecting first and second physiological instrument components, the first component having an exterior first surface and the second component having an exterior second surface, the apparatus comprising:
means forming a first connector in the first surface;
means forming a second connector in the second surface, the second connector comprising means forming a slot sized and spaced such that the first connector can be inserted in a downward direction into the slot to thereby connect the components;
latch means for selectively latching the first connector in the slot, the latch means comprising a latch arm pivotally mounted for rotation between a latching position in which the first connector is held in the slot, and an unlatched position in which the first connector can be moved out of the slot;
means adapted to exert a force on the latch arm tending to move the latch arm to the latched position; and
an actuator coupled to the latch arm by a resilient member, the stiffness of the resilient member being selected such that when the first component is supported while the second component is unsupported, movement of the actuator is insufficient to overcome the frictional force holding the latch arm in the latching position.

* * * * *